United States Patent [19]
Eisenberg

[11] 3,938,051
[45] Feb. 10, 1976

[54] DIGITAL ELECTROCARDIOGRAM WAVEFORM GENERATOR

[75] Inventor: Robert M. Eisenberg, Derwood, Md.

[73] Assignee: The Singer Company, New York, N.Y.

[22] Filed: Oct. 1, 1974

[21] Appl. No.: 511,052

[52] U.S. Cl. .................... 328/187; 328/14; 328/61; 328/143
[51] Int. Cl.² .......................................... H03K 4/00
[58] Field of Search ......... 328/14, 142, 143, 60, 61, 328/178, 187

[56] References Cited
UNITED STATES PATENTS

| | | | |
|---|---|---|---|
| 3,323,068 | 5/1967 | Woods | 328/61 X |
| 3,500,213 | 3/1970 | Ameau | 328/14 |
| 3,736,363 | 5/1973 | Baessler et al. | 328/187 X |
| 3,835,403 | 9/1974 | Leinemann | 328/14 X |
| 3,838,414 | 9/1974 | Wiles | 328/14 X |

Primary Examiner—John S. Heyman
Attorney, Agent, or Firm—William Grobman; James C. Kesterson

[57] ABSTRACT

This invention is a system for generating electrocardiogram waveforms which can be used for many purposes. The system provides a counter whose outputs are applied to a group of gates in different combinations. The outputs from the gates are applied to an integrating circuit which converts the pulse amplitude and the widths of the outputs from the gates into analog signals whose slopes depend upon the widths of the pulses applied to the integrator. Any type of cardiogram can be analyzed initially and broken into its components. These individual components and their sequence determine the connections from the outputs of the counter to the inputs of the gates.

8 Claims, 4 Drawing Figures

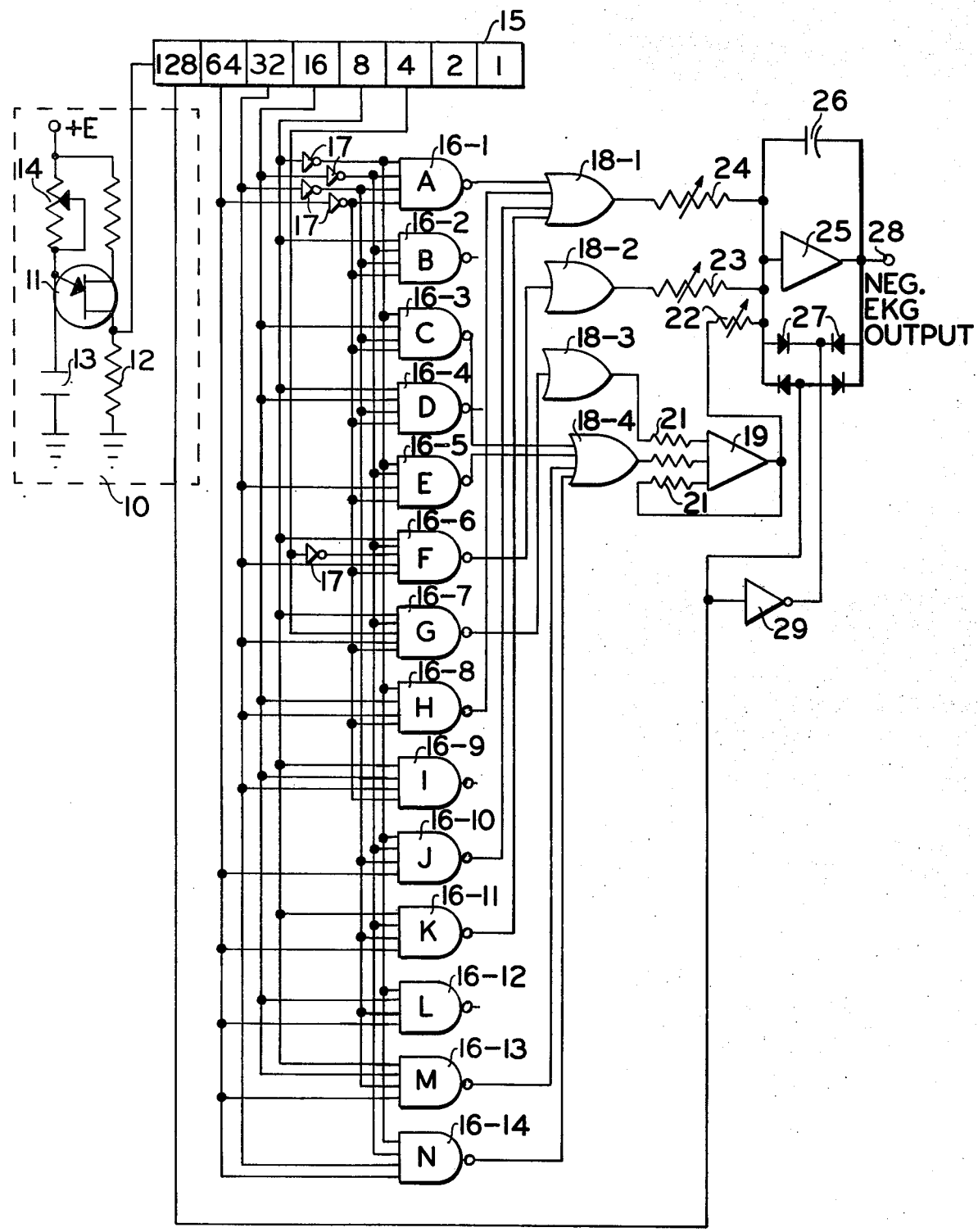
F I G. 1

3,938,051

DIGITAL ELECTROCARDIOGRAM WAVEFORM GENERATOR

BACKGROUND OF THE INVENTION

Since the beginning of World War II there has been a shortage of doctors in the world. Various means have been suggested and tried to overcome this shortage including the training of paramedics, the construction of additional instruction facilities, and similar programs. In the end, it comes down to the fact that we must train more medical specialists each year. The construction of additional instructional facilities is not enough since these facilities must also be staffed and equipped. Because of the great costs involved and because the faculties for additional instructional facilities come from the medical field and further deplete the ranks of medical practitioners, it has become apparent that more efficient ways of training medical personnel are required.

Mannikins which simulate some of the bodily functions and duplicate abberations thereof have been developed in recent years to aid in medical training. In addition to the mannikins, other simulators of medical equipment problems will improve the efficiency with which medical personnel are trained.

SUMMARY OF THE INVENTION

This invention relates to electronic devices, and more particularly to devices for simulating the operation of medical equipment.

Simulators and similar training devices are finding greater use every day, particularly for training individuals to perform complex jobs. The training of medical personnel readily falls within that general type of subject. However, until very recently, few simulators have been used for that purpose.

This invention comprises a counter which is driven by a free-running pulse generator. The outputs from the various stages of the counter are applied to the inputs of a plurality of gates which generate outputs spaced in time in dependence upon the occurrence of the outputs from the various stages of the counter. The resulting pulses are then applied to an integrator which produces an output voltage dependent upon the amplitude and time-duration of the pulses applied to it.

It is an object of this invention to provide a new and improved signal generating system.

It is another object of this invention to provide a new and improved system for producing selected waveforms.

It is a further object of this invention to provide a new and improved system for generating and modifying waveforms.

It is still another object of this invention to provide a new and improved system for generating the waveform of an electrocardiogram.

Other objects and advantages of this invention will become apparent as the following description proceeds, which description should be considered together with the accompanying drawings.

BRIEF DESCRIPTION OF THE DRAWINGS

FIG. 1 is a logic-block diagram of a waveform generator in accordance with this invention.

DESCRIPTION OF A PREFERRED EMBODIMENT

Figure 2:
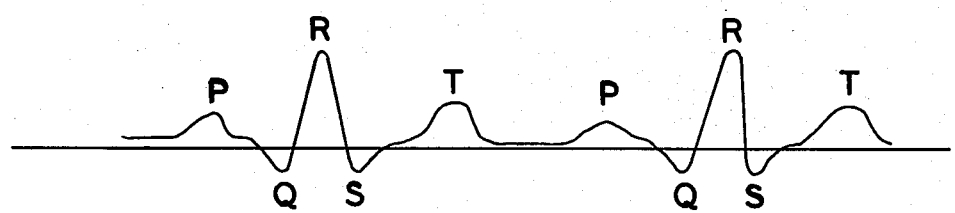
FIG. 2 is a waveform of a typical electrocardiogram.

Referring to the drawings in detail and more particularly to FIG. 1, the reference character 10 designates a free-running pulse generator which comprises a uni-junction transistor 11 having its drain electrode connected to ground through a load-resistor 12. The gate electrode of the transistor 11 is connected to a source of positive potential through a potentiometer 14 and to ground through a capacitor 13. The output of the transistor 11 is taken across the resistor 12 and is applied to the count input of a digital counter 15. The outputs from several of the stages of counter 15 are applied directly to some of the inputs of gates 16-1, 16-2, 16-3, 16-4, 16-5, 16-6, 16-7, 16-8, 16-9, 16-10, 16-11, 16-12, 16-13, and 16-14, and to other inputs of the gates 16 through inverters 17. The outputs from the AND gates 16-1 through 16-14 are connected in combination to the inputs of OR gates 18-1 through 18-4. The output from gate 18-1 is applied through a variable resistor 24 to the input of an integrator amplifier 25. The output from the gate 18-2 is applied through a variable resistor 23 to the input of the amplifier 25; the output from the gate 18-3 and the output from the gate 18-4 are applied through resistors 21 to two inputs of an amplifier 19. The output of the amplifier 19 is fed back to a third input through another resistor 21. The output of the amplifier 19 is also applied through a variable resistor 22 to the input of the amplifier 25. Connected across the amplifier 25 is an integrating capacitor 26 and also reversely connected diodes 27. The output of the highest stage of the counter 15 is connected to the diodes 27 directly and through an inverter 29. The output from the amplifier 25 is a negative version of the EKG waveform which is applied to terminal 28.

Figure 4:
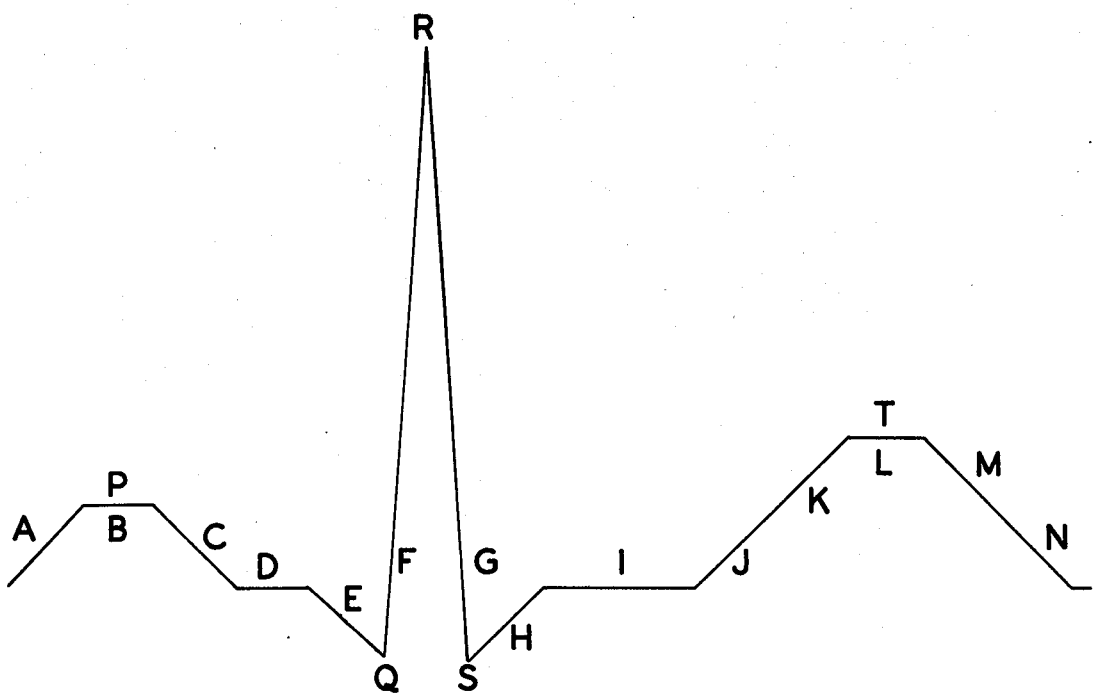
FIG. 4 is a stylized representation of one pulse of a typical electrocardiogram.

To explain the operation of this invention, reference will be made to FIGS. 2 and 4. FIG. 2 is a portion of an electrocardiogram. Perhaps it should be explained that an electrocardiogram is a graph made by an electrical instrument which moves a pen transversely across a strip of chart paper which is moving longitudinally. The excursions of the pen are determined by electrical currents produced by electrodes placed on the body at selected points. The currents produced by the electrodes correspond to the action of the heart in its operation. Since the heart is a cyclically operating member, the cardiogram is a repetitious curve. Each cycle of the curve should be identical to each other cycle, and the basic curve should conform, generally, to the curve shown in FIG. 2 and labeled P, Q, R, S, T. Variations in one or more of the labeled portions of the curve indicate problems with the particular circulatory system represented by the electrocardiogram. The apparatus of this invention is designed to produce the curve of FIG. 2. To aid in an analysis of the curve, a stylized version of one cycle is shown in FIG. 4. Each portion of the curve of FIG. 4 is labeled with one letter of the alphabet A–N. The apparatus of FIG. 1 is designed to produce each of the individual portions of the curve of FIG. 4.

As can be seen from FIG. 4 the curve of the electrocardiogram comprises fourteen parts, each with its own length and slope. In the apparatus of FIG. 1 the gates 16-1 – 16-14 are labeled A–N and correspond to the fourteen portions of the curve in FIG. 4. The oscillator 10, which comprises the uni-junction transistor 11, potentiometer 14, and capacitor 13, oscillates at a rate which is proportional to the standard heartbeat rate. The individual pulses are applied to the counter 15 and step that counter through its count. The outputs from the counter 15 correspond to the standard binary numbering system. Thus, the first pulse produces an output from the stage farthest to the right. The next pulse produces an output from the stage immediately to the left of the first stage. The third count produces outputs from both the first and the second stages. As the pulses from the oscillator are applied to the counter 15 the outputs from the various stages become energized in a binary sequence. These energizations are applied to the gates 16-1 – 16-14 to cause the individual gates to open and close at prescribed times and for a selected time interval. For example, consider the gate 16-1. The outputs from the stages which represent the counts of 8, 16, 32, and 64 are applied through inverters 17 to the inputs of the gate 16-1. During the time that the counter 15 energizes these four outputs, the gate 16-1 produces an output signal which is applied to one input of the gate 18-1. The output from the gate 18-1 is applied through the variable resistor 24 to the input of the integrator formed by the amplifier 25 and the capacitor 26. The integrator produces a rising output voltage whose final amplitude is proportional to the time-duration of the pulse applied from the gate 18-1. This increasing voltage appears at the output terminal 28 producing that portion of the curve shown in FIG. 4 labeled A. Since that portion of the curve of FIG. 4 labeled B is horizontal, no output from the gate 16-2 is applied to the integrator. The inputs to the gate 16-3 are energized when the 8, the 16, and the 32 outputs from the counter 15 are energized and when the 16 output from the counter 15 is not energized. In this manner, the slope of the curve which is determined by the time that the gate 16-3 is open is the same as the slope produced by the output of the gate 16-1, but at a later time. This is accomplished by taking the same inputs that are applied to the gate 16-1 and waiting until the count 16 output decays. Since the slope of the portion C of the curve of FIG. 4 has a negative slope, the output from the gate 16-3 is applied to the input of the gate 18-4 which is a down-gate. The output from the gate 18-4 is applied through an amplifier 19 which serves to invert that segment. Thus, the output of the gate 18-4, and also of the gate 18-3, is of opposite polarity from the outputs of the gates 18-1 and 18-2. The output of the amplifier 19 is applied through the variable resistor 22 to the input of the integrator which produces a negative-going voltage having the same slope and of the same duration as the portion A. In the manner explained above in the operation of the gates 16-1, 16-2, and 16-3, the individual segments D–N of the curve of FIG. 4 are produced by the apparatus shown in FIG. 1. The amount of the slopes of several portions of the curve can be varied by changing the individual resistors 22, 23, and 24. If the portion of the curve of FIG. 4 represented by the horizontal segments B, D, I, or L are to have positive or negative slope portions, then corresponding gates 16-2, 16-4, 16-9, and 16-12 may have their outputs connected to the OR gates 18-1, 18-2, 18-3, or 18-4. Thus, the apparatus of FIG. 1 produces a waveform which corresponds to a typical electrocardiogram. In addition, the waveform produced at the output of FIG. 1 may be varied by modifying the values of the adjustable resistors 22, 23, and 24 and also by selectively connecting into or out of the circuit the outputs from the gates 16-2, 16-4, 16-9, and 16-12. The outputs from these gates may be connected to the inputs of the various series 18 gates by the use of suitable switches.

Figure 3:
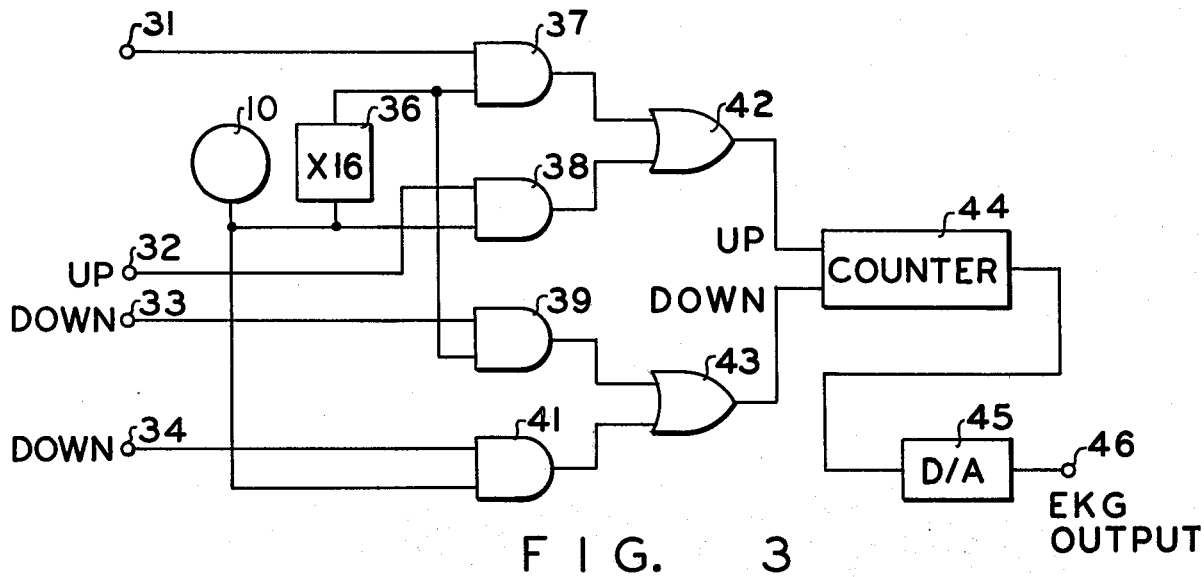
FIG. 3 is a logic-block diagram of an additional circuit provided for the output of the generator of FIG. 1.

The amplitude of the output waveform produced by the system of FIG. 1 varies somewhat with the frequency of the oscillator 10. To overcome this problem in cases where it is undesirable, the system shown in FIG. 3 can be substituted for the integrator of FIG. 1. In FIG. 3 the clock 10, which is shown in FIG. 3 but is really the same as oscillator 10 of FIG. 1, applies clock pulses directly to AND gates 38 and 41 and through a frequency multiplier 36 to one input of each of AND gates 37 and 39. The other inputs of AND gates 37, 38, 39 and 41 are directly connected to the outputs of the OR gates 18-1 – 18-4 of FIG. 1. The second input of gate 37 is connected to an input terminal 31 which is adapted to be connected to the output of gate 18-1. The second input to the gate 38 is connected to a terminal 32 which is adapted to be connected to the output of gate 18-2. The second input to the gate 39 is connected to a terminal 33 adapted to be connected to the output of gate 18-3; and the second input to gate 41 is connected to a terminal 34 which is adapted to be connected to the output of gate 18-4. The outputs of the two gates 37 and 38 are applied to the inputs of an OR gate 42. The outputs of gates 39 and 41 are connected to the two inputs of an OR gate 43. The output from gate 42 is applied to the count-up input to a reversible counter 44, and the output from gate 43 is applied to the count-down input of the counter 44. The count-output of the counter 44 is applied as digital input to a digital-to-analog converter 45 whose analog output supplies the output terminal 46 with the electrocardiogram waveform.

In order to overcome the problem of the output waveform varying with the frequency of the input signal, the apparatus of FIG. 3 is connected to the outputs of the gates 18-1 – 18-4 to substitute a digital arrangement for the integrator 25. The gates 37, 38, 39, and 41 each have two inputs, one of which is a signal input and the other of which is a clock input from the clock 10. Each of the gates 37–41 produces an output signal only when both input signals are present. Thus, the output of any of the gates 37–41 can be considered to be a high frequency rectangular wave which is modulated by the pulse output from the gates 18-1 – 18-4. Expressed in another way, when any of the gates 37–41 produces an output signal, that signal comprises the pulse from the oscillator 10 for the length of time that the pulse output from the gates 18-1 – 18-4 exists. These pulses are applied through the up-gate 42 or the down-gate 43 to the respective inputs to the counter 44. When the signals appear at the output of gate 42, they cause the counter 44 to count upwards. When a signal appears at the output of the gate 43 the output pulses cause the counter 44 to count in a downward direction. Since the count-output of the counter 44 is applied to the input of the digital-to-analog converter 45, the output of the D/A converter 45 varies with the count of the counter 44. This is an EKG output at the terminal 46. The apparatus shown in FIG. 3 is a completely digital system and is not frequency-dependent.

The above specification has described a new and improved system for generating a prescribed waveform such as that of an electrocardiogram. It is realized that the above description may indicate to others skilled in the art additional ways in which the principles of this invention may be used without departing from its spirit. It is, therefore, intended that this invention be limited only by the scope of the appended claims.

What is claimed is:

1. A waveform generator for generating a non-symmetrical recurrent waveform, said generator comprising a source of clock signals, a counter, means for connecting the output from said source to the count input of said counter, said counter having a plurality of outputs which are energized in a prescribed sequence as said counter counts clock signals from said source, a plurality of coincidence circuits, means for connecting the individual outputs from said counter to the inputs of said coincidence circuits so that individual coincidence circuits are rendered conductive at prescribed times and for prescribed intervals to generate individual potentials each of which represents a unique slope of the waveform at a prescribed time, means connected to the outputs of said coincidence circuits for receiving the signal outputs of said coincidence circuits and forming them into a continuous multisloped waveform, said means for connecting the outputs of the counter to the inputs of said coincidence circuits includes means for directly connecting the outputs of said counter to the inputs of those coincidence circuits for generating the portions of the waveform having a slope in one direction, and means including inverters for connecting the inverted outputs from the counter to those coincidence circuits which generate the portions of the waveform having a slope of opposite polarity to said one direction.

2. The generator defined in claim 1 wherein said means connected to the outputs of said coincidence circuits comprises an integrator.

3. The generator defined in claim 2 further including adjustable means connected between the outputs of said coincidence circuits and the inputs to said integrator for changing the slopes of selected portions of said waveform output from said integrator.

4. The generator defined in claim 3 wherein said means connected to the outputs of said coincidence circuits includes adjustable means of changing the slopes of said portions.

5. The generator defined in claim 4 wherein said means connected to the outputs of said coincidence circuits includes an integrator.

6. The generator defined in claim 1 wherein said means connected to the outputs of said coincidence circuits includes a counter, a digital-to-analog converter having its input connected to said counter for receiving the count output of said counter and converting said count into an equivalent waveform, and means between the outputs of said coincidence circuits and the input to said counter for providing the count input of said counter with signals from said source of clock signals modulated by the outputs of said coincidence circuits.

7. The generator defined in claim 1 wherein said means connected to the outputs of said coincidence circuits comprises a counter, a digital-to-analog converter having its input connected to said counter for receiving the count output of said counter and converting said count into an equivalent waveform, and means between the outputs of said coincidence circuits and the input to said counter for providing the count input of said counter with signals from said source of clock signals modulated by the outputs of said coincidence circuits.

8. The generator defined in claim 4 wherein said means connected to the outputs of said coincidence circuits includes a counter, a digital-to-analog converter having its input connected to said counter for receiving the count output of said counter and converting said count into an equivalent waveform, and means between the outputs of said coincidence circuits and the input to said counter for providing the count input of said counter with signals from said source of clock signals modulated by the outputs of said coincidence circuits.

* * * * *

UNITED STATES PATENT AND TRADEMARK OFFICE
CERTIFICATE OF CORRECTION

PATENT NO. : 3,938,051
DATED : February 10, 1976
INVENTOR(S) : Robert M. Eisenberg It is certified that error appears in the above-identified patent and that said Letters Patent are hereby corrected as shown below:

Column 5, line 29, after "the inverted outputs from the counter", change "to" to -- through --.

Signed and Sealed this

Twenty-fourth Day of May 1977

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,938,051
DATED : February 10, 1976
INVENTOR(S) : Robert M. Eisenberg It is certified that error appears in the above-identified patent and that said Letters Patent are hereby corrected as shown below:

Column 2, line 19, change "AND gates" to -- NAND gates --.

Signed and Sealed this

Fourth Day of April 1978

[SEAL]

Attest:

RUTH C. MASON
Attesting Officer

LUTRELLE F. PARKER
Acting Commissioner of Patents and Trademarks